United States Patent

Skaletz

[11] Patent Number: 4,457,810
[45] Date of Patent: Jul. 3, 1984

[54] 4,4'-DIPHENYL ETHER-DIALDEHYDE-BIS-DIMETHYLACETAL AND A PROCESS FOR ITS PREPARATION

[75] Inventor: Detlef H. Skaletz, Mainz, Fed. Rep. of Germany

[73] Assignee: Hoechst Aktiengesellschaft, Frankfurt am Main, Fed. Rep. of Germany

[21] Appl. No.: 412,246

[22] Filed: Aug. 27, 1982

Related U.S. Application Data

[62] Division of Ser. No. 333,013, Dec. 21, 1981, Pat. No. 4,405,816.

[30] Foreign Application Priority Data

Dec. 24, 1980 [DE] Fed. Rep. of Germany ....... 3048992

[51] Int. Cl.³ .............................................. C25C 1/00
[52] U.S. Cl. .................................................. 204/59 R
[58] Field of Search ....................................... 204/59 R

[56] References Cited

U.S. PATENT DOCUMENTS 4,284,825  8/1981  Degner .............................. 204/59 R
4,318,783  3/1982  Buhmann ........................... 204/59 R

*Primary Examiner*—John F. Niebling
*Attorney, Agent, or Firm*—Schwartz, Jeffery, Schwaab, Mack, Blumenthal & Koch

[57] ABSTRACT

Disclosed is the novel compound 4,4'-diphenylether-dialdehyde-bis-dimethylacetyl of the formula

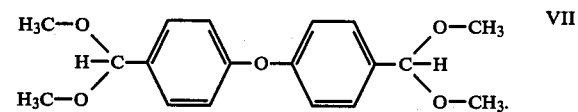

and a process for its preparation from di-p-tolyl ether

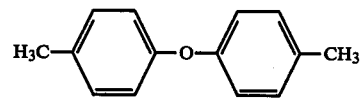

by anodic oxidation of the latter in the presence of methanol and of a supporting electrolyte. The anode material used in this reaction is preferably platinum, lead dioxide, graphite or vitreous carbon, and the cathode material used is preferably steel, nickel, or graphite. The supporting electrolyte used is preferably $NaOCH_3$, KOH, $KPF_6$, CsF, $NaBF_4$, $LiBF_4$, tetraethylammonium p-toluenesulfonate, $H_2SO_4$ or $CH_3OSO_3H$, individually or as a mixture.

8 Claims, No Drawings

4,4'-DIPHENYL ETHER-DIALDEHYDE-BIS-DIMETHYLACETAL AND A PROCESS FOR ITS PREPARATION

This is a division of application Ser. No. 333,013, filed Dec. 21, 1981, now U.S. Pat. No. 4,405,816.

BACKGROUND OF THE INVENTION

The present invention relates to 4,4'-diphenyl ether-dialdehyde-bis-dimethylacetal and to a process for its preparation.

It is known that anodic alkoxylation of unsubstituted or substituted methylbenzenes of the general formula (I) can lead to the corresponding benzaldehydedialkylacetals of the general formula (II):

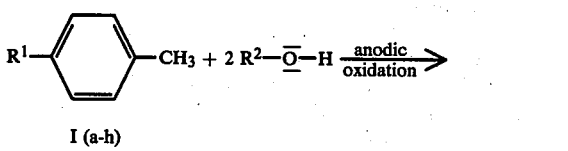

I (a-h)

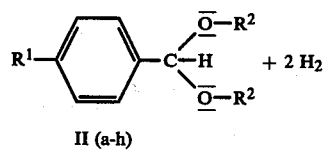

II (a-h)

| REACTANT | R¹ | R² | PRODUCT |
|---|---|---|---|
| I a | H | CH₃ | II a |
| b | CH₃ | CH₃ | b |
| c | O—CH₃ | CH₃ | c |
|  |  | C₂H₅ | c' |
| d | O—CH₂—C₆H₅ | CH₃ | d |
| e | O—CH₂—CH=CH₂ | CH₃ | e |
| f | O—C₆H₅ | CH₃ | f |
| g | O—t-C₄H₉ | CH₃ | g |
| h | O—C(O)—N(CH₃)₂ | CH₃ | h |

According to the article "Anodic Methoxylation of Alkylbenzenes" by K. Sasaki, H. Urata, K. Uneyama and S. Nagaura in *Electrochimica Acta*, 1967, Vol. 12, pp. 137–146, toluene (Ia) is converted on platinum electrodes in methanol to benzaldehyde-dimethylacetal (IIa) (or, after hydrolysis, to benzaldehyde itself) and to methyl benzyl ether. According to the data in F. Beck, *Elektroorganische Chemie*, Verlag Chemie-Weinheim, 1974, page 248, the yield of (IIa) is said to be about 10% of the theoretical.

Published French Patent Application No. 2,351,932 describes the electrochemical oxidation of methylbenzenes, such as toluene (Ia) and xylene (Ib). The following products are obtained in the oxidation of toluene (Ia) in an electrolyte system composed of methanol and a co-solvent, such as methylene chloride, with the use of acidic supporting electrolytes and after subsequent hydrolysis: methyl benzyl ether, benzaldehyde and p-methoxybenzaldehyde, and in addition also, inter alia, o-methoxy-benzaldehyde or p-methoxytoluene. The yields of benzaldehyde are 3.6 to 13.2% of the theoretical. In the corresponding anodic oxidation of p-xylene (Ib), the reaction products (no yield data are given) are methyl-p-xylyl ether, 4-methyl-benzaldehyde, methyl-4-methyl-benzoate and 2-methoxy-4-methyl-benzaldehyde.

According to the article "Anodic Substitution and Addition Reactions" by S. Tsutsumi and K. Koyama in *Discussions of the Faraday Society*, 1968, No. 45, pp. 247–253, ring-substituted methoxy derivatives of toluene or of tolunitrile are also obtained in the anodic cyanation of toluene on platinum electrodes in a methanol/NaCN system.

More recently, remarkable increases in the selectivity of the electrochemical alkoxylation of toluenes substituted in the 4-position have also been disclosed.

In the article "Nuclear Cyanation of Methylanisoles" by k. Yoshida, M. Shigi and T. Fueno in *J. Org. Chem.*, 1975, Vol. 40, No. 1, pp. 63–66, the reaction of 4-methoxytoluene (Ic) in a methanolic solution of NaCN or Na acetate is described. In this reaction, 4-(methoxymethyl)-anisole and, in a material (current) yield of 15% (24%) of the theoretical, anisaldehyde-dimethylacetal (IIc) are also formed, in addition to the respective ring-substitution products.

A. Nilsson, U. Palmquist, T. Pettersson and A. Ronlan, "Methoxylation of Methyl-substituted Benzene and Anisole Derivatives, and the Synthesis of Aromatic Aldehydes by Anodic Oxidation" in *J. Chem. Soc., Perkin Transactions I*, 1978, pp. 708–715, have succeeded in methoxylating p-xylene (Ib) and 4-methoxytoluene (Ic) in methanol with the use of NaOCH₃/LiBF₄ or NaOCH₃ supporting electrolytes on a carbon anode at about 10° C. to give compound (IIb) in a material (current) yield of 57% of the theoretical and compound (IIc) in a material (current) yield of 66% of the theoretical.

In Published European Application No. 0,011,712 (see also German Offenlegungsschrift No. 2,848,397), benzaldehyde-dialkylacetals, substituted in the 4-position, of the general formula

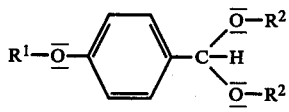

are described, wherein R¹, inter alia, can also represent a phenyl radical or benzyl radical and R² can represent an alkyl radical having 1 to 4 C atoms. These compounds are prepared by electrochemically oxidizing methylbenzenes (toluenes), substituted in the 4-position, of the general formula

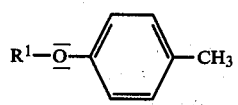

in the presence of an alcohol $$R^2-\underline{O}-H$$

(R[1] and R[2] having the meaning indicated above) and of a supporting salt. Examples of suitable supporting salts are: fluorides such as KF, tetrafluoborates such as Et$_4$NBF$_4$ (where Et=ethyl), perchlorates such as Et$_4$N-ClO$_4$, sulfates such as Et$_4$NSO$_4$Et, alcoholates such as NaOCH$_3$ and hydroxides such as KOH. The quantitative proportions of the components should be between about 5 and 50% by weight of the substituted methylbenzenes, between about 50 and 95% by weight of the alcohol and between about 0.5 and 15% by weight of the supporting salt. Graphite, graphite-filled plastics and noble metals are mentioned as the anode materials, and graphite, iron, steel, lead and noble metals are mentioned as the cathode materials. The current densities are from 1 to 20 A/dm$^2$, and the electrolysis temperature is between about 0° and 60° C. In detail, the anodic methoxylation or ethoxylation, respectively, of p-xylene (Ib) gives a material yield (current yield) of 32% (18%) of the theoretical of 4-methyl-benzaldehyde-dimethylacetal (IIb), that of 4-methoxytoluene (Ic) gives 42.4% (22%) to 73.1% (56.5%) of anisaldehydedimethylacetal (IIc) or 53.4% (—) of anisaldehydediethylacetal (IIc'), that of 4-benzyloxytoluene (Id) gives 62.1% (47.9%) of 4-benzyloxy-benzaldehyde-dimethylacetal (IId), that of 4-allyloxytoluene (Ie) gives 36.3% (10.8%) of 4-allyloxy-benzaldehyde-dimethylacetal (IIe), that of 4-phenoxy toluene (If) gives 39.2% (14.3%) of 4-phenoxy-benzaldehyde-dimethylacetal (IIf), that of 4-t-butoxytoluene (Ig) gives 52.5% (19.2%) of 4-t-butoxy-benzaldehyde-dimethylacetal (IIg) and that of 4-N,N-dimethylamino-carboxyl-toluene gives 40.4% (—) of 4-(N,N-dimethylamino-carboxy)-benzaldehyde-dimethylacetal.

In the process for the preparation of substituted benzaldehyde-dialkylacetals according to Published European Application No. 0,012,240, inter alia, methylbenzenes (toluenes), substituted in the 4-position, of the general formula

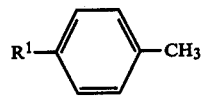

in which R[1] can, inter alia, represent an aryloxy or aralkoxy radical, are electrochemically oxidized in solution in an alcohol of the formula $$R^2-\underline{O}-H$$

(R[2]=alkyl) and in the presence of a supporting salt at a current density of 0.1 to 50 A/dm$^2$. The aryloxy and aralkoxy radicals mentioned are, inter alia, phenoxy, naphthyloxy, anthryloxy, benzyloxy and 2-phenylethoxy, according to which p-phenoxytoluene (=1-methyl-4-phenoxy-benzene) should then, inter alia, also be included with the methylbenzenes substituted in the 4-position. Suitable supporting salts include tetraethylammonium-p-toluene-sulfonate, tetraethylammonium-ethyl-sulfate or tetramethylammonium dimethyl phosphate. Graphite, lead dioxide and noble metals are mentioned as anode materials, and copper, nickel, steel, platinum and graphite are mentioned as cathode materials. In detail, the anodic methoxylation of p-xylene (Ib) gives a material yield (current yield) of 64% (—) of 4-methylbenzaldehyde-dimethylacetal (IIb), that of 4-methoxytoluene (Ic) gives 67% (71%) to 95% (—) of 4-methoxybenzaldehyde-dimethylacetal and that of 4-t-butoxytoluene (Ig) gives 55% (—) to 92% (—) of 4-t-butoxybenzaldehyde-dimethylacetal (IIg).

None of these numerous publications, however, contains even the slightest hint to the effect that it would be possible to alkoxylate aromatic compounds which have 2 methyl groups located on an aromatic system in the molecule, to simultaneously alkoxylate both methyl groups to give the corresponding aromatic dialdehyde-bis-dialkylacetals. Thus, for example, as described by A. Nilsson et al. (cited above), the anodic oxidation of p-xylene (Ib), depending on the experimental conditions (page 709, bottom of right-hand column) either leads via a nuclear methoxylation to 1-methyl-1-methoxy-4-methyl-4-methoxy-cyclohexa-2,5-diene (III) or leads via a side-chain methoxylation to (4-methyl-benzyl)-methyl-ether (IV), to 4-methylbenzaldehyde-dimethylacetal (IIb) or, in the last oxidation stage, to the ortho-ester of p-toluic acid (V):

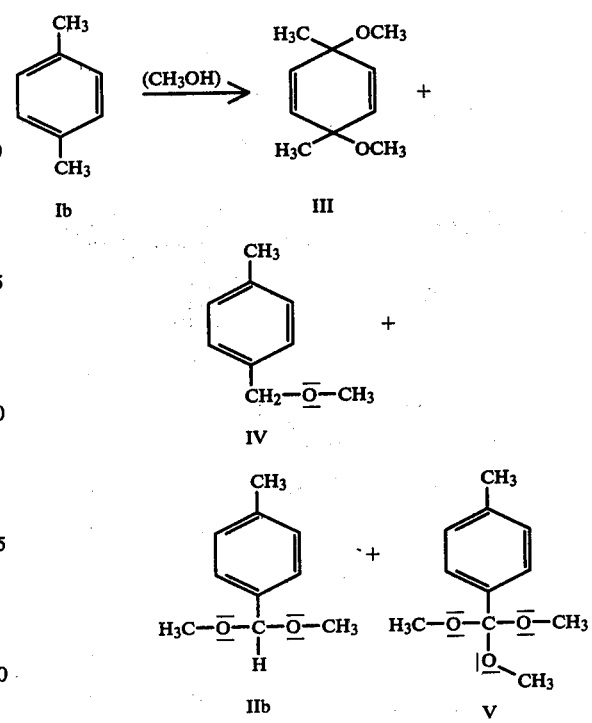

The even more recent publications (German Offenlegungsschrift No. 2,848,397, European Application No. 0,011,712 or European Application No. 0,012,240) likewise do not contain any hint to the effect that, in the anodic methoxylation of, e.g., p-xylene (Ib), even traces of terephthaldialdehyde-bis-dimethylacetal (VI)

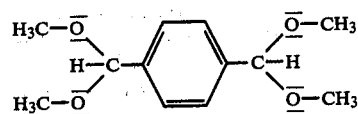

could be formed. Even with the most sensitive analytical methods, such as a combination of gas chromatography and mass spectroscopy according to Published French Application No. 2,351,932, it was not possible to detect either the dialdehyde or the corresponding bis-dimethylacetal in this reaction.

These findings coincide with the results in an article "Anodic Oxidation of Arylcyclopropanes" by T. Shono and Y. Matsumura in *J. Org. Chem.*, 1970, Vol. 35, No. 12, pp. 4157–4160, according to which either an α-methoxylation to give 2-(p-tolyl)-2-methoxypropane, or the secondary product p-isopropenyl-toluene obtained therefrom, or an α'-methoxylation to give (p-i-propylbenzyl)-methyl-ether takes place in the anodic methoxylation of 4-i-propyltoluene. Accordingly, once a methoxy group has entered into the α-position, a possible subsequent α'-substitution in the same molecule is completely inhibited.

SUMMARY OF THE INVENTION

It is the therefore an object of the present invention to provide a process for the preparation of bis-dimethylacetals.

It is also an object of the invention to produce a symmetrical bis-dimethylacetal, namely, 4,4'-diphenyl ether-dialdehyde-bis-dimethylacetal, by an anodic methoxylation reaction.

In accomplishing the foregoing objects, there has been provided in accordance with the present invention a new compound, 4,4'-diphenyl ether-dialdehyde-bis-dimethylacetal, having the formula

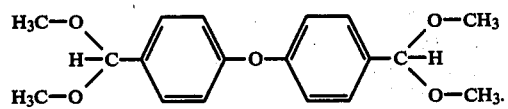

In accordance with another aspect of the invention, there has been provided a process for the preparation of the foregoing compound which comprises the step of anodically oxidizing di-p-tolyl ether of the formula

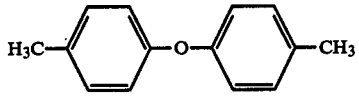

in the presence of methanol and a supporting electrolyte. Preferably, the supporting electrolyte comprises NaOCH$_3$, KOH, KPF$_6$, CsF, NaBF$_4$, LiBF$_4$, tetraethylammonium p-toluenesulfonate, H$_2$SO$_4$, CH$_3$OSO$_3$H, or a mixture thereof. Most preferably, the supporting electrolyte is a type such that, after the electrolysis has ended, it can be converted into a compound which is insoluble or does not dissociate in methanol.

Further objects, features and advantages of the present invention will become apparent from the detailed description of preferred embodiments which follows.

DETAILED DESCRIPTION OF PREFERRED EMBODIMENTS

The invention relates to the new compound 4,4'-diphenyl ether-dialdehyde-bis-dimethylacetal (VII)

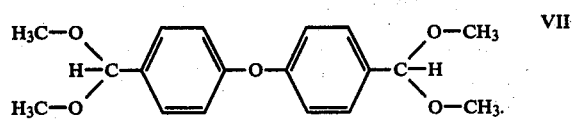

This compound is prepared by anodically oxidizing di-p-tolyl ether (VIII) in the presence of methanol and of a conducting electrolyte. The reaction can be represented as follows:

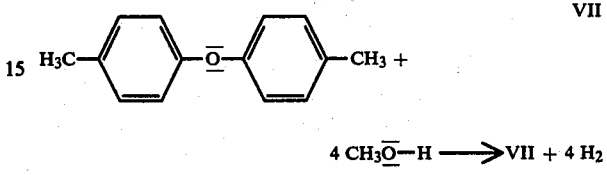

$$4 \, CH_3\overline{O}-H \longrightarrow VII + 4 \, H_2$$

For the first time in a surprising manner, contrary to the previous findings and expectations, this enables an aromatic compound having 2 methyl groups located on an aromatic system to be anodically methoxylated on both sides, that is partially and at the same time symmetrically, in such a way that the compound (VII) is obtained as the reaction product. The process for the preparation of this compound (VII) represents a modification of the process described by A. Nilsson et al. (cited above).

The process according to the invention can be carried out in the known pressure cells or flow cells of undivided construction, optionally with stirring or with pumped circulation of the electrolyte. The flow velocity of the electrolyte is of rather subordinate importance and can be varied between about 5 cm/second and 10 m/second without significantly impairing the reaction. The anode materials used are the materials customary in organic electrochemistry, such as platinum, lead dioxide, graphite or vitreous carbon. Metal-free anodes are preferred. The cathode materials used are the customary solids, such as steel, nickel or graphite, and materials having a low cathodic hydrogen overvoltage are preferred. The form of the anodes and cathodes is of minor importance and, for example, plates, rods, spheres or even structured shapes can be used.

The anode current densities can be varied within the range from about 5 mA/cm$^2$ (0.5 A/dm$^2$) up to about 500 mA/cm$^2$ (50 A/dm$^2$), and the range between about 50 and 200 mA/cm$^2$, in particular, a range between about 50 and 100 mA/cm$^2$, is preferred.

The supporting electrolytes which can be used for the process according to the invention are those customary in organic electrochemistry. These include, in particular, NaOCH$_3$, KOH, KPF$_6$, CsF, NaBF$_4$, LiBF$_4$, tetraethylammonium p-toluenesulfonate, H$_2$SO$_4$ or CH$_3$OSO$_3$H. Perchlorates, such as, for example, LiClO$_4$, are unsuitable in practice. The supporting electrolytes can be used either individually or as a mixture. Those supporting electrolytes are preferred in the process according to the invention which, after the electrolysis has ended, can be converted into an insoluble or non-dissociating compound by the addition of a suitable auxiliary substance which is as anhydrous as possible. For example, supporting electrolytes, such as H$_2$SO$_4$ or NaOCH$_3$, can be converted into such an "inactive" compound with stoichiometric quantities of NaOCH$_3$ or H$_2$SO$_4$, respectively. This possibility of "inactivating" the supporting electrolyte is especially important whenever, after the electrolysis has ended, the reaction mixture containing the bis-dimethylacetal as an intermediate is to be directly processed further to give end products which are to be modified chemically. In this case, additional working-up stages can then be omitted. This process variant is particularly advantageous in the homogeneous hydrogenation, described below, as a possibility for direct further processing of the bis-dimethylacetal. The concentration of the supporting electrolyte or electrolytes is advantageously within the range of from about 0.01 to 20% by weight, preferably from about 0.05 to 5% by weight, relative to the total electrolyte.

The reactant in the process according to the invention, namely di-p-tolyl ether, can be present in the electrolyte in a concentration of from about 1 to 40% by weight, relative to the total electrolyte. The solvent used for the process according to the invention is methanol in the anhydrous form, or alternatively, a technical grade having a small water content of, for example, about 0.2 to 0.3% by weight. The electrolysis temperature can vary within wide limits, and in general it should be betweeen about 10° C. and 65°° C., that is to say approximately between room temperature and the boiling point of the electrolyte mixture.

The reaction batch can be worked up by one of the conventional procedures, for example, by distillation or filtration. Preferably, however, it should be carried out with exclusion of moisture, so that the bis-dimethylacetal formed according to the invention is not hydrolyzed to the bis-aldehyde. The supporting electrolytes and solvents, which are obtained by such working-up of the reaction batch and are thus recoverable, can be re-used in subsequent batches not only without problems, but with particular advantage. In one variant of the process according to the invention, as already described above, the supporting electrolytes are converted into "inactive compounds" so that the reaction mixture can be directly processed further to give further products.

In the process according to the invention, in particular at a current conversion of about 8 to 12 Faradays/mole, almost exclusively 4,4'-diphenyl ether-dialdehyde-bis-dimethylacetal is obtained from the di-p-tolyl ether. By contrast, at a current conversion of about 4 Faradays/mole, only a very inhomogeneous product mixture of 6 compounds, namely, unconverted di-p-tolyl ether and the side-chain substitution products monomethoxy-, symmetrical dimethoxy-, asymmetrical dimethoxy-, trimethoxy- and tetramethoxy-di-p-tolyl ether, is obtained.

The process according to the invention, by producing a high degree of upgrading, opens up to a new route to an industrially important compound, namely 4,4'-bis-methoxy-methyl-diphenyl ether (IX).

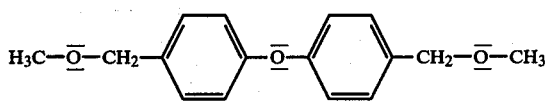

IX

This compound is of importance, in particular, in the preparation of aromatic polyethers from hydroxymethyldiaryl ethers or alkoxymethyl-diaryl ethers. (See, for example, German Pat. No. 1,252,903 or U.S. Pat. No. 3,316,186.) These aromatic polyethers are suitable as a binder in the preparation of casting compositions or as an adhesive in the production of laminates. Another known use of the compound (IX) is its reaction, described in German Offenlegungsschrift No. 2,065,732 (=U.S. Pat. No. 3,867,147) with aromatic diazonium compounds to give light-sensitive condensation products from these two components. The preparation of (IX) by homogeneous catalytic hydrogenolysis of 4,4'-diphenyl ether-dialdehyde-dimethylacetal, the compound according to the invention, in methanol in the presence of a soluble cobalt carbonyl catalyst modified with organic nitrogen bases is described in detail in U.S. Pat. No. 4,413,149.

In the examples which follow, unless stated otherwise, % data are by weight. Parts by weight have the same relationship to parts by volume as the kg to the $dm^3$.

EXAMPLE 1

The electrolytic cell used is an undivided flow cell of polyethylene with minimized electrode spacing, wherein the geometrical cathode and anode areas are 0.1 $m^2$, the electrode separation is 1 mm and the flow velocity of the electrolyte is 0.8 m/second. Devices for keeping the temperature constant, for taking samples, or the like, are located in the electrolyte circulation outside the cell. Commercially available apparatus grade graphite impregnated with synthetic resin (Diabon-N from Sigri Elektrographit GmbH, Meitingen) is used as the anode, and a commercially available electrolysis graphite (EH type from the same manufacturer) is used as the cathode. The electrolyte is composed of 4,040 parts by weight (5,100 parts by volume) of technical grade methanol, 29.2 parts by weight of incompletely dissolved $NaBF_4$ and 595 parts by weight of di-p-tolyl ether. The molar ratios are 0.266 mole of conducting salt per 3 moles of reactant. The other reaction conditions are: a temperature of 45° C., a current density of 50 $mA/cm^2$, a cell current of 50 A, a cell voltage of 7.3 to 7.7 V and a current conversion of 9.2 Faradays/mole corresponding to 740 ampere-hours (=115%).

After the reaction has ended, the methanol is distilled off, with exclusion of moisture, over a packed column (main fraction under normal pressure, and the remainder in a vacuum of about 20 to 40 mm Hg), the distillation residue is stirred with 2,000 parts by volume of dry diethyl ether, and the precipitated conducting salt is filtered off with suction. After the residue is washed with dry diethyl ether and is dried, 27.6 g (=94.5% of the theoretical) of the conducting salt are recovered. The diethyl ether is removed from the reaction product by distillation, and 829.3 g of distillable constituents are separated off from 65.2 g of non-volatile, resinous constituents in a thin-layer evaporator (oil circulation temperature 250° C., oil pump vacuum 0.01 to 0.2 mm Hg).

The gas-chromatographic analysis (GC) of the distillate [10% strength in methanol, 1.5 m of Silikon OV 225: 25% of phenyl, 25% of cyanopropyl, methyl on 80 to 100 mesh Chromosorb G AW DMS (manufacturer: John Manville Products), 60 ml of He/minute, 80° C. start, 8°/minute] shows 90.4 area-% of compound (VII), namely, 4,4'-diphenyl ether-dialdehyde-bis-dimethylacetal. In addition to the mass spectrum (molecular mass 318), the elementary analysis Found: C 67.4%; H 6.8%; O 24.4%. Calculated: C 68.1%; H 6.7%; O 25.2%.

and the highly symmetrical $^1$H-NMR spectrum (60 Mhz in $CDCl_3$) with

C-H (acetal) 12 H, S, 3.3 ppm,
C-H (aldehyde) 2 H, S, 5.32 ppm and
C-H (aromatic, 1,4-disubstituted) 8 H, AA'BB' system, 7.2 ppm prove the presence of the bis-dimethylacetal according to the invention.

EXAMPLE 2

The electrolytic cell used is an undivided flow cell of polyethylene with a minimized electrode separation. The cell contains 1 VA steel end cathode, 1 end anode of vitreous carbon (Sigradur K) and 4 bipolar center electrodes of vitreous carbon/VA steel (manufacturer of the commercially available electrodes: Sigri Elektrodengraphit GmbH, Meitingen). The electrode separation is defined by 1 mm thick polyethylene grids, the anode and cathode areas are each $5 \times 255$ cm$^2$, i.e., a total of 1,275 cm$^2$ each, and the flow velocity is set to 0.8 m/second. Devices for keeping the temperature constant, for taking samples, and the like, are located in the electrolyte circulation outside the cell. The electrolyte is composed of 12,750 parts by volume of technical grade methanol, 30 parts by volume of concentrated H$_2$SO$_4$ and 595 parts by weight of di-p-tolyl ether. The other reaction conditions are: a temperature of 18° C., a current density of 100 mA/cm$^2$, a cell current of 25.5 A, a cell voltage of 34 to 38 V and a current conversion of 10.6 Faradays/mole corresponding to 852 ampere-hours (=132%).

After the reaction has ended, the conducting electrolyte is neutralized with 61 parts by weight of NaOCH$_3$ (in methanol solution) and the electrolyte is worked up in accordance with the instructions of Example 1 and analyzed by gas chromatography, according to which the high-boiling compounds, which can be separated off, contain 89.7% of compound (VII).

After clarification by filtration, the neutralized electrolyte, without the working-up indicated in Example 1, can be successfully processed further directly, for example, in the homogeneous catalytic hydrogenolysis reaction described in the above-mentioned U.S. Pat. No. 4,413,149.

What is claimed is:

1. A process for the preparation of 4,4'-diphenyl ether-dialdehyde-bis-dimethylacetyl having the formula

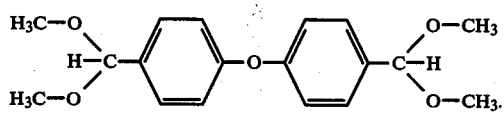

which comprises the steps of:
(a) providing a mixture comprising methanol, a supporting electrolyte, and di-p-tolyl ether of the formula

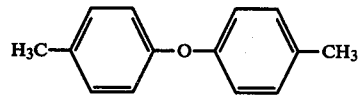

(b) anodically oxidizing said di-p-tolyl ether in said mixture using a current conversion of between about 8 and 12 Faradays/mole of said di-p-tolyl ether.

2. A process as claimed in claim 1, wherein the anode material used in said anodic oxidation step (b) comprises platinum, lead dioxide, graphite or vitreous carbon, and the cathode material comprises steel, nickel or graphite.

3. A process as claimed in claim 1, wherein said supporting electrolyte comprises NaOCH$_3$, KOH, KPF$_6$, CsF, NaBF$_4$, LiBF$_4$, tetraethylammonium p-toluenesulfonate, H$_2$SO$_4$, CH$_3$OSO$_3$H, or a mixture thereof.

4. A process as claimed in claim 1, wherein said supporting electrolyte is capable, after the electrolysis has ended, of being converted into a compound which is insoluble or does not dissociate in methanol.

5. A process as claimed in claim 4, wherein said supporting electrolyte comprises H$_2$SO$_4$ or NaOCH$_3$.

6. A process as claimed in claim 1, wherein the anode current density is from about 5 to 500 mA/cm$^2$, and the electrolysis temperature is between about 10° C. and 65° C.

7. A process as claimed in claim 6, wherein the anode current density is from about 50 to about 200 mA/cm$^2$.

8. A process as claimed in claim 1, wherein said mixture comprises from about 1 to about 40% by weight of di-p-tolyl ether and from about 0.01 to 20% by weight of supporting electrolyte, relative to the total electrolyte.

* * * * *